United States Patent [19]

Sun

[11] Patent Number: 5,824,543
[45] Date of Patent: Oct. 20, 1998

[54] METHOD FOR EXPRESSION AND ISOLATION OF BIOLOGICALLY ACTIVE MOLECULES IN URINE USING A MOUSE UROPLAKIN-II PROMOTER

[75] Inventor: Tung-Tien Sun, Scarsdale, N.Y.

[73] Assignee: New York University, New York, N.Y.

[21] Appl. No.: 464,961

[22] Filed: Jun. 5, 1995

[51] Int. Cl.$^6$ .......................... C07H 21/04; C12N 15/09; C12N 15/63; C12N 15/00
[52] U.S. Cl. ..................... 435/320.1; 435/172.3; 435/69.1; 436/24.1; 935/23; 935/34
[58] Field of Search ............... 435/320.1, 172.3, 435/69.1; 536/24.1; 935/23, 34

[56] References Cited

FOREIGN PATENT DOCUMENTS

WO 94/05782  9/1993  WIPO .

OTHER PUBLICATIONS

Garver et al., Gene Therapy, 1(1):46–50, 1994.
Meyer–Puttlitz et al., Neuro Report, 6:1674–1678, 1995.
Lin et al., PNAS USA, 92:679–683, 1995.
Frohman et al., "Rapid production of full–length cDNAs from rare transcripts: Amplification using a single gene–specific oligonucleotide primer", *Proc. Nat'l Acad. Sci. USA* 1988, 85, 8998–9002.
Hicks, R.M., "The Fine Structure of the Transitional Epithelium of Rat Ureter", *J. Cell Biol.* 1965, 26, 25–48.
Hicks, R.M., "The Mammalian Urinary Bladder: An Accommodating Organ", *Biol. Rev.* 1975, 50, 215–246.
Koss, L.G., "The Asymmetric Unit Membranes of the Epithelium of the Urinary Bladder of the Rat", *Lab. Invest.* 1969, 21, 154–168.
Lin et al., "Precursor Sequence Processing, and Urothelium–specific Expression of a Major 15–kDa Protein Subunit of Asymmetric Unit Membrane", *J. Biol. Chem.* 1994, 269, 1775–1784.

Mercer et al., "The Dopamine β–Hydroxylase Gene Promoter Directs Expression of E. coli lacZ to Sympathetic and Other Neurons in Adult Transgenic Mice", *Neuron* 1991, 7, 703–716.
Peschon et al., "Spermatid–specific expression of protamine 1 in transgenic mice", *Proc. Natl. Acad. Sci. USA* 1987, 84, 5316–5319.
Ryan et al., "Chromosomal localization of uroplakin genes of cattle and mice", *Mamm. Genome* 1993, 4, 656–661.
Staehelin, L.A., "Lumenal Plamsa Membrane of the Urinary Bladder", *J. Cell Biol.* 1972, 53, 73–91.
Wu, X.–R. and Sun, T.–T., "Molecular cloning of a 47 kDa tissue–specific and differentiation–dependent urothelial cell surface glycoprotein", *J. Cell Sci.* 1993, 106, 31–43.
Wu et al., "Large Scale Purification and Immunolocalization of Bovine Uroplakins I, II, and III", *J. Biol. Chem.* 1990, 265, 19170–19179.
Wu et al., "Mammalian Uroplakins", *J. Biol. Chem.* 1990, 265, 19170–19179.
Wu et al., "Uroplakins Ia and Ib, Two Major Differentiation Products of Bladder Epithelium, Belong to a Family of Four Transmembrane Domain (4TM) Proteins", *J. Biol. Chem.* 1994, 269, 13716–13724.
Yu, J., "Uroplakin I: A 27–kD Protein Associated with the Asymmetric Unit Membrane of Mammalian Urothelium", *J. Cell Biol.* 1994, 125, 171–182.

*Primary Examiner*—Brian R. Stanton
*Attorney, Agent, or Firm*—Law Offices of Jane Massey Licata

[57] ABSTRACT

A recombinant nucleic acid construct is presented in which a mouse uroplakin-II (UP-II) gene promoter is coupled to a heterologous gene of interest. When the resultant construct is introduced into a transgenic mouse, the UP-II promoter directs the expression of the heterologous gene in the urothelium of the said mouse.

1 Claim, 4 Drawing Sheets

FIG. 1b-2

```
631  TAATGCCTTGCCCCCATGTCACCTGCACGGGAGGTAATGCCACATTGATGGTCCGGAGAGCCAACGACAGCAAAGGTAGACCTCCCTTGT
      I  A  L  P  P  C  H  L  T  G  G  N  A  T  L  M  V  R  R  A  N  D  S  K  V L→2

721  ACCCATTTATTCTACTCGTCGTAACCCTCTTAACGATACCCAAGAGCTGCCCCGTTCTACAGAGTGGACGCTAGAATCTGATCTTGCCT

811  TTCACTCCTATTTCCCCTAGTGGTTAAGTCAGACTTTGTGGTCCTCCATGTCGCGGGCGCAGGGAGCTTGTGAGCGTGGTGGACAGTG
                                              V  P  P  C  R  G  R  R  E L→
                                                                        *

901  GGTCTGGCTACACCGTCACCAAGGCTCAGGCGCCATATCAGGTGACAAACCTAACACCAAATACTAGTAGTACCGATGACACCT
      S  G  Y  T  V  T  R  L  S  A  Y  Q  V  T  N  L  T  P  G  T  K  Y  Y L→3

991  GTGGAGGTGGGATGGCAAAAAAGGGAGTTGGAGGTCCCGTGAGGGTGGGAAGTGCCGGGAAGCATGAGTTAGAGAGGGCACAGCTAAAG

1081 GGTAGGAAATGTGAACCTGGACCCCCAGAGGGGACACATAGCTAGAAGGTGGAGGCTGGAACCCCTCCCGAGTGCCAG

1171 ATACGTACAACCTCTGCTTTCTCTCCAACTCCGCCTCTAAAGCATATCCTACCGAGTACAGAAGGGACGTCAGTCCAGAG
         I  S  Y  R  V  Q  K  G  T  S  T  E  S  S  P  E

1261 ACTCCCATGTCCACGCTTCCTCCGTTAAGTAAAATGCCCGTCTCTCACACTTTTTCTCCTAGAGCAAGTTAGCT
      T  P  M  S  T  L  P  R L→4

1351 AAACTGTTTCCCGAGTGCTCAGTGCACACACCCCCCCAACCACCCCCCCAGTATTTGGTATGCCCCTCCTGTTCAATCATCT

1441 CTGCACTAGAGGTTCCTTGTGCAGAGGAATGATGTCCTCCTCCTTGGTGCCTCCTAAGTGTCCTCTATGTTGCTTGACTG

1531 GTTGGCTGGATGACCAGTTGAACTGGACAGTTCCCCCATGTCTGAGGCTAATGCTGTGAACCACAGAGCTACCTAGGAACCCCTT

1621 CAACTCACAGAGTTCCCCATGTCTTCTTCTGACAGAAAAAACATGAGTCTATTGGGTTAGAAACAATGGCCCGACCAGAGGATGGTGGT
                                              K  N  M  E  S  I  G  L  G  M  A  R  T  G  G  M  V  V
                                          4→

1711 CATCACAGTGCTGCTGTCTGTGGCCATGTTCCTGTTGGTCGTGGGTCTCTTATTGTTGCCCTGCACTGGATGCCCGCAAATGAAAGGGCT
      I  T  V  L  L  S  V  A  M  F  L  L  V  V  G  L  I  V  A  L  H  W  D  A  R  K  *

1801 CTCCTGCATCCCAGCTCCTCCAAGAAGTCCAGCTGCCCTCCCTGCCAGGCTGTAGTCACTGGCTTCTCAGTGGCTTTCTCCCTCTCCC

1891 CGCCCCCTCCTCGAGTCCTCCACTCCTGACAGTGCCCCCTCCCTGCAGCACTCCCTGTCTCACCTTGACCCACGTAGTGTCTCTGACTG

1981 GCCAACACTGATTTATCTCTTAACTGTACTTAATTCTCACAATAAAGGCTAGTTAATTCTCACATATCAAAACTACCAATGTCAAGCT

2071 AGTCACCCCTTTAGCTGCTGGTCCCCTTATGCAGGAGGCAAGCAGGACAGAGATAATGAAGCCTCAAGCTAGGAACCCTCCAAGCCCCA

2161 AGGGTGACTTTTTACCAGGAGGCAAGCAGCTAGGACTCGCACTCAGTAAGCCTCAGTGGGGCAGGGAAGCTGGATCACCATGTGAGCCT

2251 AGGGCTTGGGTTTGCATCCTGCACTCAGTAACCCAAGCAGTAGATACCCAGCAGGGCAGGCCCCAGCCTGGGTGAAGAACAGCAGTGCT

2341 GACTGGGAAGCTGACAGAACTGAGGTGACGGAAGCTCCTGGAAGGGACACAACATAGGTAAACAGGCACCCTCGTCC

2431 TCTAGACCCCTGAGCTGACAGAATATAGTTTTGTTCTATAAAGTTTTATTTATTTGCTGTTTGTTGTTTCCAGAGCTGAGG

2521 ATTTTTAAAATATAGTTTTGTTCTATAAAGTTTTATTTATTTGCTGTTTGTTGTTTCCAGAGCTGAGG

2611 CAAAAACCCAGAGCTTGAGCTTGCTAGGCAAGCTAAATCCCCACTGAGCTCTACCACTGAGTGCTCTACCACTGAGTTTTTTGAAGCAGGGTT

2701 TCTCTGTGTAGCTCTGGCTGTCCTACAGCTC  2731
```

METHOD FOR EXPRESSION AND ISOLATION OF BIOLOGICALLY ACTIVE MOLECULES IN URINE USING A MOUSE UROPLAKIN-II PROMOTER

INTRODUCTION

This invention was made in the course of research sponsored by the National Institutes of Health. The U.S. Government may have certain rights in this invention.

BACKGROUND OF THE INVENTION

Urothelium, also known as transitional epithelium, is a multilayered epithelium that covers the surface of much of the urogenital tract including the renal pelvis, ureter, the entire bladder and a portion of the urethra. The apical surface of urothelium, in direct contact with the urine, is covered with numerous rigid looking plaques. These plaques cover a large portion of the apical surface of mammalian urothelium. Hicks, R. M. *J. Cell Biol.* 1965, 26, 25–48; Koss, L. G. *Lab. Invest.* 1969, 21, 154–168; Staehelin, L. A. *J. Cell Biol.* 1972, 53, 73–91. They are believed to play a crucial role as a permeability barrier (Hicks, R. M. *Biol. Rev.* 1975, 50, 215–246) and/or as physical stabilizer of the urothelial cell surface (Staehelin, L. A. *J. Cell Biol.* 1972, 53, 73–91). When viewed in cross section, the outer leaflet of the plaque is almost twice as thick as the inner one, hence the term "asymmetrical unit membrane" or "AUM" has been used to describe these plaques.

It has recently been shown that AUM contain 4 major integral membrane proteins which are called uroplakin Ia (UPIa; 28 kDa), uroplakin Ib (UPIb; ~27 kDa), uroplakin II (UPII; 15 kDa) and uroplakin III (UPIII; 47 kDa). EM-immunolocalization studies established that these uroplakins are AUM-associated in situ, thus establishing them as the major protein subunits of urothelial plaques. Yu et al. *J. Cell Biol.* 1990, 111, 1207–1216; Wu et al. *J. Biol. Chem.* 1990, 265, 19170–19179. Immunohistochemical survey of various bovine tissues established that these UPs are urothelium-specific being present in the upper cell layers of the urothelia that cover the urogenital tract including the renal pelvis, ureter, bladder and part of the urethra. These data established uroplakins as excellent markers for an advanced stage of urothelia differentiation. Yu et al. *J. Cell Biol.* 1990, 111, 1207–1216; Wu et al. *J. Biol. Chem.* 1990, 265, 19170–19179. Furthermore, uroplakins Ia, Ib, II and III appear to be the major protein components of all mammalian urothelial plaques. They are found in eight other mammalian species (human, monkey, sheep, pig, dog, rabbit, rat, and mouse), and the AUMs of these species appear morphologically similar, bearing crystalline patches of 12-nm protein particles with a center-to-center spacing of 16.5 nm. Wu et al. *J. Biol. Chem.* 1994, 269, 13716–13724.

The primary structures of UPs have recently been elucidated by cDNA cloning. The results established the existence of two closely related UPI isoforms, the 27-kDa UPIa and the 28-kDa UPIb. Yu, J. *J. Cell Biol.* 1994, 125, 171–182. The mRNAs of all four known UPs have recently been shown to be urothelium-specific, indicating that expression of UP genes is transcriptionally regulated. Yu, J. *J. Cell Biol.* 1994, 125, 171–182; Lin et al. *J. Biol. Chem.* 1994, 269, 1775–1784; Wu, X. -R. and Sun, T. -T. *J. Cell Sci.* 1993, 106, 31–43.

The expression of the mouse UPII gene, like its bovine counterpart, is urothelium- and late-differentiation stage-specific. Using transgenic mouse techniques, a 3.6-kb 5' flanking region has now been identified as a promoter comprising the cis-elements for directing the expression of a heterologous reporter gene specifically and efficiently to the suprabasal cell layers of the urothelium in a manner similar to the endogenous UPII gene. Using this promoter, it has now been found that foreign proteins can be directed to the upper cell layers of the bladder urothelium for expression and secretion into urine.

SUMMARY OF THE INVENTION

An object of the present invention is to provide a method for expressing biologically active molecules in the luminal cavity of the bladder of transgenic animals for subsequent excretion and recovery from urine wherein expression of the gene encoding the biologically active molecule is targeted to and driven by a class of urothelial-specific promoters that drive, for example, uroplakin-related genes to express in the upper cell layers of urothelia. The sequence of the 3.6 kB upstream promoter region of mouse uroplakin II gene is provided.

Another object of the present invention is to provide a method of producing transgenic animals containing urothelial promoter-driven heterologous genes encoding biologically active molecules.

Yet another object of the present invention is to provide a method for producing a biologically active molecule which comprises producing a transgenic animal which expresses a selected biologically active molecule in bladder epithelial cells and recovering the biologically active molecule from urine produced by the transgenic animal.

BRIEF DESCRIPTION OF THE FIGURES

FIG. 1a provides the exon-intron organization of mouse UPII gene. The open and filled thick boxes denote the five coding sequences (exons) and non-coding sequences (introns), respectively, of the gene. The open and filled thin boxes represent a $(CA)_n$ dinucleotide repeat region and an Alu-like murine B1 repeat, respectively. G1 and G2 designate two independent and partially overlapping genomic clones. The restriction sites are SacI (S), NcoI (N), BamHI (B), SalI (Sal), and XhoI (X).

FIG. 3a provides a restriction map (abbreviations as described in FIG. 1) of the endogenous murine UPII gene. A 500-bp PCR fragment (thick bar) was used as a probe which detects a 1.4-kb NcoI fragment of the endogenous UPII genome but a shorter 1.1-kb NcoI fragment of the transgene.

DETAILED DESCRIPTION OF THE INVENTION

Two major problems of producing biologically active molecules such as protein products from cloned genes on a commercially viable scale are: (1) that bacterial expression systems frequently fail to modify the proteins properly, i.e., by glycosylation, etc., and (2) the subsequent isolation of gene products from the expression systems. In bacteria, yeast, and baculovirus systems the expressed proteins are most often purified from insoluble intracellular compartments. Secreted proteins in yeast require specialized protease-deficient strains coupled with appropriate vectors with secretion signals. More recently, there has been success in using mammary gland-specific promoters to drive the expression of foreign proteins in these secretory glands, ultimately leading to their secretion in the resultant milk. This method has been used commercially to express human growth hormone in cows and sheep. WO 94/05782. The copious volumes of milk produced by cows and sheep make this procedure attractive. However, this method suffers from several potential drawbacks: one being that the expressed protein even at relatively high levels must be purified away from a large amount of milk proteins such as caseins, immunoglobins, lactoferrins which may also entrap the desired valuable product; another being that certain protein products may be insoluble in the calcium-rich environment of milk fluid; and another being that this method requires the use of pregnant animals which are expensive and time consuming to produce.

In the present invention, a method has been developed for expressing biologically active molecules in the luminal cavity of the bladder of transgenic mammals. Urine in the bladder is of relatively high osmolality (50 to 1,000 mosmol/kg), with pH values as low as 4.5, and contains high concentrations of urea and ammonium. The lumen of the bladder may therefore provide an advantageous environment for the production of proteins that are normally difficult to express due to insolubility. The urea and high osmolality may serve as in situ denaturants and chaotropic agents. However, urine contains relatively little protein, in comparison with milk, as the kidneys are designed to prevent protein loss, therefore urothelial promoter-driven expression of proteins which by-passes the kidney produces the desired protein in a solution with relatively little contaminating host endogenous proteins.

Figure 1:
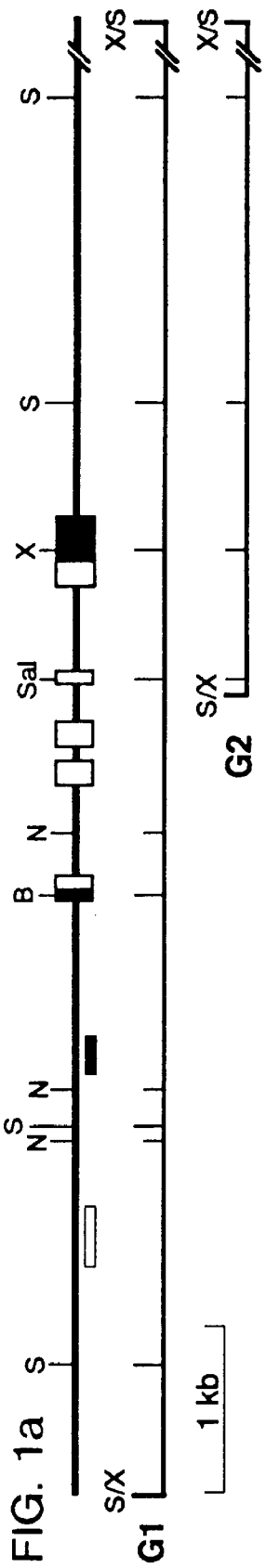
FIGS. 1a and b show is the organization and nucleotide sequence of the mouse uroplakin II (UPII) genomic DNA.
FIG. 1b provides the nucleotide sequence (SEQ ID NO: 1) of a 4-kb SacI fragment of mouse UPII gene. A reversed B1 repetitive sequence (in the 5' upstream region) and a potential polyadenylation site (AATAAA; in the 3' untranslated region) are underlined and double-underlined, respectively. The wavy arrow denotes the transcriptional initiation site. Broken arrows marked 1 to 4 denote the intron/exon junctions of the four introns. The predicted first amino acid residue of mature UPII protein sequence is marked with an asterisk. The preceding domain contains a pre and a pro sequence of 25 and 59 amino acids, respectively.

The promoter region of the uroplakin II gene has now been elucidated. Using a bovine UPII cDNA as a probe, a 16-kb mouse genomic clone (G1) was isolated which contains an ~2.5-kb transcribed region that is flanked by ~3.5-kb and ~10 kb of 5'- and 3'- sequences, respectively (see FIG. 1a). Alignment of the coding sequence with the UPII cDNA sequences of cattle (Lin et al. *J. Biol. Chem.* 1994, 269, 1775–1784), which are highly homologous, defined the exon/intron junctions of four introns (FIG. 1b). 5'-RACE (Frohman et al. *Proc. Nat'l Acad. Sci. USA* 1988, 85, 8998–9002) experiments using mouse bladder mucosal mRNA as a template established that the transcription site of the UPII gene is located at 60-bp 5'-upstream of the translation initiation codon and 27-bp downstream of a putative TATA box. The 5'-upstream region contains an Alu-like B1 repetitive sequence (–830 bp) and a $(CA)_n$ stretch (~–2.1 kb). Finally, a polyadenylation signal resides ~230 bp downstream of the translation stop codon (see FIG. 1b).

Figure 2:
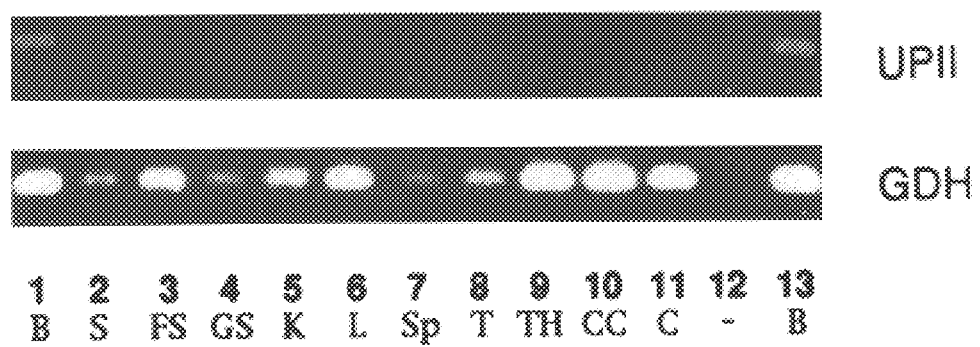
FIG. 2 illustrates the tissue distribution of UPII mRNA as assayed by RT-PCR. Poly(A)+mRNAs (0.3–0.4 mg) from mouse bladder (lanes 1 and 13), skin (2), forestomach (3), glandular stomach (4), kidney (without renal pelvis) (5), liver (6), spleen (7), testis (8), and thalamus/hypothalamus (9), cerebral cortex (10), and cerebellum (11) regions of the brain were reverse-transcribed, and amplified with either UPII-specific primers (Upper; 266 bp) or glyceraldehyde-3-phosphate dehydrogenase (GDH)-specific primers (Lower, as an internal control for comparison; 130 bp). The PCR products were then electrophoresed on a 1.3% agarose gel and stained with ethidium bromide. Lane 12 is a negative control (no cDNA template). The 266-bp UPII product was detected in abundance in bladder, but not in any other tested tissues, including the hypothalamus.

The mouse UPII gene is urothelium-specific like the bovine UPII gene. mRNAs were prepared from various mouse tissues and probed for the presence of UPII sequences by reverse transcription-polymerase chain reaction (RT-PCR) assay. A large amount of UPII product of expected size (266-bp) was generated from the bladder, but not from skin, forestomach, glandular stomach, kidney, liver, spleen, testis, or the hypothalamus/thalamus cortex and cerebellum of the brain (see FIG. 2).

A rabbit antiserum previously prepared against a synthetic peptide corresponding to the N-terminal amino acid sequence ELVSVVDSGSG (1–11) (SEQ ID NO: 2) of mature bovine UPII (Lin et al. J. Biol. Chem. 1994, 269, 1775–1784) immunohistochemically stains the 15-kDa bovine UPII and localizes it to the superficial cell layers of bovine urothelium. This antiserum cross-reacted well with mouse UPII, which contains an identical epitope, but migrates slightly slower at an apparent 17 kDa mass. Immunofluorescent staining of frozen sections of mouse bladders showed that the UPII was associated with the all the suprabasal cell layers, suggesting that the onset of UPII gene expression in mouse was earlier than that in cattle.

Figure 3A:
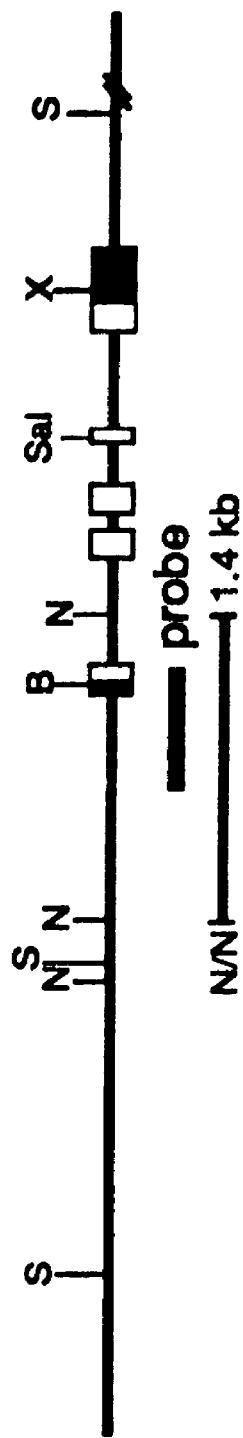
FIGS 3a and b illustrate the construction and quantitation of a representative transgene.
Figure 3B:
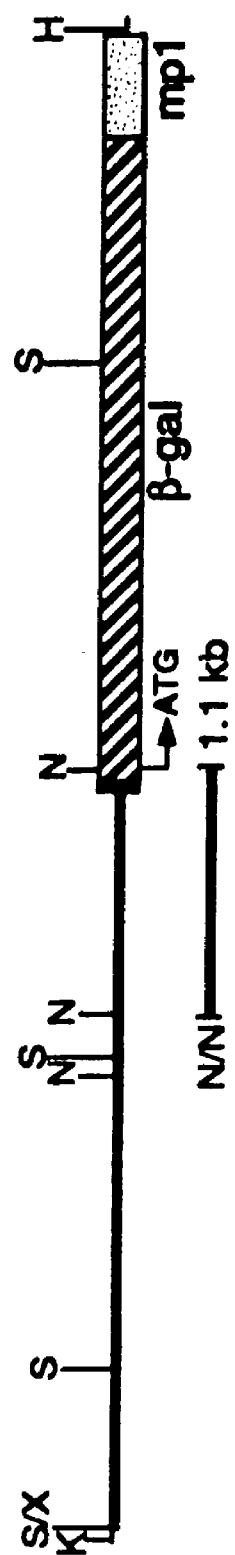
FIG. 3b provides a restriction map of the transgene. A 3.6-kb 5'-flanking sequence of the UPII gene was inserted into an *Escherichia coli* β-galactosidase (β-gal)-encoding placF vector. In this particular test expression vector, a sequence containing a part of exon 1 and all of intron 1 and exon 2 of the mouse protamine-1 gene (mp1) was placed at the 3'-end of the β-gal (or lacZ) gene to provide an exon/intron splicing site and a polyadenylation signal. This chimeric gene was cut out from the vector, gel-purified, and microinjected into mouse eggs.

To define the cis promoter elements for urothelial-specific expression and to demonstrate that heterologous genes can be targeted to the suprabasal urothelial cells as endogenous UPII, a transgenic mouse was constructed that contains a chimeric gene in which a lacZ reporter gene was under the regulation of a 3.6-kb 5'-flanking sequence of the mouse UPII gene (FIG. 3b). The DNA construct was injected into fertilized mouse eggs for transgenic mouse production. Southern blot analyses of the tail DNAs showed that the transgene was integrated into the genomes of 4 of 25 mice. Three of these animals transmitted the reporter gene into their progeny. Southern blot analyses established that the genomic DNAs of these three transgenic lines, TG1, TC2, and TG3, contained roughly 40, 6, and 30 copies, respectively, of the reporter gene per diploid genome. Probing the same Southern blot with the lacZ sequence showed that the transgenes of all three lines were in tandem repeats and were integrated into independent sites.

In all three mice lines, the transgene was expressed in the suprabasal cells of the bladder epithelium in an expression pattern similar to the endogenous UPII gene. The staining correlated somewhat with gene dosage, as it was intense in TG1 (40 copies) but moderate in TG2 (6 copies) and TG3 (30 copies). β-galactosidase activity was only observed in the bladder and other urothelia of mice that had inherited the transgene, confirming that the activity was transgene-specific. In all three transgenic mice, no β-galactosidase activity was detected in any of the non-urothelial stratified epithelia tested, including those of the skin, tongue, cornea, esophagus, and forestomach. The reporter gene product was also undetectable in all other epithelia tested, including those of liver, lung, glandular stomach, small and large intestine, uterus, and testis; or mesenchymal tissues, including fibroblasts, endothelial cells, spleen, and various muscle cells.

Other urothelia closely related to the epithelium of the bladder known to cover other areas of the urinary tract, such as the renal pelvis of the kidney, the ureter, and the urethra and which also elaborate AUM plaques, exhibit similar expression of the transgene.

These data show that the 3.6-kb 5'-flanking sequence of the mouse UPII gene can drive a heterologous reporter gene to express in the upper cell layers of the bladder epithelium. The lack of expression in other non-urothelial tissues indicates a high degree of tissue-specificity and demonstrates that the cis elements of this promoter region provide very tight regulatory control on tissue-specific and differentiation-dependent expression of a gene placed downstream of the promoter. As these results were corroborated in three independent transgenic lines with differing sites of transgene integration, they show that the inherent promoter activity is responsible for the tissue-specific expression and is not due to the effect of neighboring sequences of the transgene integration sites. This tight regulation is a very desirable property of any promoter used for production of foreign protein products in host transgenic animals, as it assures correct delivery to target production sites, high efficiency of expression of transduced genes, and minimizes toxic effect of aberrant expression.

While these experiments were conducted using the mouse UPII promoter, there is sufficient similarity between this gene in different species, so that similar results with the UPII promoter sequence in other animals is expected. For example, the UP gene organization (Ryan et al. *Mamm. Genome* 1993, 4, 656–661), cDNA (Lin et al. *J. Biol. Chem.* 1994, 269, 1775–1784) and protein sequences, tissue patterns of expression, and morphology of AUMs are strikingly similar between the mouse and cow. The amino acid sequence of bovine and mouse UPII are highly similar, sharing 84 of their 100 amino acid residues. Wu et al. *J. Biol. Chem.* 1994, 269, 13716–13724. In addition, although the onset of expression of the UPII gene is different in these two species, UPII is clearly differentiation-related in both cow and mouse bladder epithelia.

In the present invention, a delivery system is provided that can specifically transform the bladder into a bioreactor capable of making a transgenic product. This delivery system comprises a transgene containing a 3.6-kb 5'-flanking sequence of a urothelium-specific gene, for example, the mouse uroplakin II gene, and a gene encoding a biologically active molecule. In one embodiment, this transgene is introduced into germ cells to produce a transgenic animal capable of expressing the biologically active molecule in its bladder. As used herein, "biologically active molecule" refers to a molecule capable of causing some effect within an animal, not necessarily within the animal having the transgene. Examples of such molecules include, but are not limited to, adipokinin, aldosterone, adrenocorticotropin, blood clotting factors, chorionic gonadotropin, corticoliberin, corticotropin, cystic fibrosis transmembrane conductance regulators, erythropoietin, folliberin, follitropin, glucagon gonadoliberin, gonadotropin, hypophysiotropic hormone, insulin, lipotropin, luteinizing hormone-releasing hormone, luteotropin, melanotropin, parathormone, parotin, prolactin, prolactoliberin, prolactostatin, somatoliberin, somatotropin, thyrotropin, tissue-type plasminogen activator, and vasopressin. Of course, as will be obvious to one of skill in the art, the above list is not exhaustive. In addition, new genes for biologically active molecules that will function in the context of the present invention are continually being identified. The biologically active molecule can be isolated from the urine of these transgenic animals. Accordingly, the present invention provides a means for isolating large amounts of biologically active molecules from the urine of transgenic animals which can be used for a variety of different purposes.

In another embodiment, the transgene is carried in a vector which is well received by the epithelial cells lining the lumen of the bladder. An example of a useful vector system is the Myogenic Vector System (Vector Therapeutics Inc. Houston Tex.). In this embodiment, the transgene carried in the vector is introduced into the bladder of an animal in vivo. Introduction of the vector can be carried by a number of different methods routine to those of skill in the art. For example, a vector of the present invention could be placed in direct contact with the urothelium via a rubber urethral catheter or Foley catheter. Vectors of the present invention can also be incorporated into liposomes and introduced into the animal in that form. The transgene is absorbed into one or more epithelial cells capable of expressing and secreting the biologically active molecule into the urine collecting in the bladder. It may be preferred for some biologically active molecules to also engineer a signaling sequence into the vector to insure that the molecule is secreted from the apical surface into the lumen. Use of signaling sequences such as the glycophosphatidylinositol (GPI) linkage in anchoring molecules to a selected surface is well known in the art. The biologically active molecule is then voided from the lumen where it can be collected and separated from other components in the urine.

The following nonlimiting examples are provided to further illustrate the present invention.

EXAMPLES

Example 1

Characterization of the Mouse UPII Gene

A bovine UPII cDNA (Lin et al., *J. Biol. Chem.* 1994, 269, 1775–1784) was used as a probe to screen a mouse EMBL3-SP6A/T7 genomic library (Clontech Laboratories Inc. Palo Alto, Calif.). Two overlapping clones (G1 and G2) were isolated (FIG. 1*a*) and were sequenced by the dideoxynucleotide termination method. The transcriptional initiation site was determined by sequencing three clones of 5'-RACE (rapid amplification of cDNA ends) products of mouse bladder cDNA.

Example 2

Expression of a Fusion Gene (UPII-lacZ) in Transgenic Mice

A 6-kb XhoI DNA fragment of the G1 genomic clone (FIG. 1*a*) was subcloned in pGEM7Z and then restriction-cut to yield a 3.6-kb DNA fragment of G1 clone (extending from the XhoI site at −3.6 kb to the BamHI site at −42 bp relative to the transcription initiation site) and inserted into the SmaI site of a lacZ vector, placF, (Peschon et al. *Proc. Natl. Acad. Sci. USA* 1987, 84, 5316–5319; Mercer et al. *Neuron* 1991, 7, 703–716) to generate pUPII-LacZ (FIG. 3). The 7.1-kb fusion gene was excised using Kpn I and Hind III, gel-purified, and microinjected into fertilized mouse eggs (from F1 hybrids of C57BL/6J×DBA2), which were implanted into CD-1 foster mothers. The lacZ transgene was identified by Southern blot analysis of tail DNA in accordance with methods well known in the art. Positive founder animals were back-crossed with (C57BL/6J×DBA2) F1 hybrids to generate semizygous animals that were used for studying transgene expression.

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 3963
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO: 1:

| | | | | | |
|---|---|---|---|---|---|
| GAGCTCAGGT | CCTATCGAGT | TCACCTAGCT | GAGACACCCA | CGCCCCTGCA | 50 |
| GCCACTTTGC | AGTGACAAGC | CTGAGTCTCA | GGTTCTGCAT | CTATAAAAAC | 100 |
| GAGTAGCCTT | TCAGGAGGGC | ATGCAGAGCC | CCCTGGCCAG | CGTCTAGAGG | 150 |
| AGAGGTGACT | GAGTGGGGCC | ATGTCACTCG | TCCATGGCTG | GAGAACCTCC | 200 |
| ATCAGTCTCC | CAGTTAGCCT | GGGGCAGGAG | AGAACCAGAG | GAGCTGTGGC | 250 |
| TGCTGATTGG | ATGATTTACG | TACCCAATCT | GTTGTCCCAG | GCATCGAACC | 300 |
| CCAGAGCGAC | CTGCACACAT | GCCACCGCTG | CCCCGCCCTC | CACCTCCTCT | 350 |
| GCTCCTGGTT | ACAGGATTGT | TTTGTCTTGA | AGGGTTTTGT | TGTTGCTACT | 400 |
| TTTTGCTTTG | TTTTTTCTTT | TTTAACATAA | GGTTTCTCTG | TGTAGCCCTA | 450 |
| GCTGTCCTGG | AACTCACTCT | GTAGACCAGG | CTGGCCTCAA | ACTCAGAAAT | 500 |
| CCACCTTCCT | CCCAAGTGCT | GGGATTAAAG | GCATTCGCAC | CATCGCCCAG | 550 |
| CCCCCGGTCT | TGTTTCCTAA | GGTTTTCCTG | CTTTACTCGC | TACCCGTTGC | 600 |
| ACAACCGCTT | GCTGTCCAAG | TCTGTTTGTA | TCTACTCCAC | CGCCCACTAG | 650 |
| CCTTGCTGGA | CTGGACCTAC | GTTTACCTGG | AAGCCTTCAC | TAACTTCCCT | 700 |
| TGTCTCCACC | TTCTGGAGAA | ATCTGAAGGC | TCACACTGAT | ACCCTCCGCT | 750 |
| TCTCCCAGAG | TCGCAGTTTC | TTAGGCCTCA | GTTAAATACC | AGAATTGGAT | 800 |
| CTCAGGCTCT | GCTATCCCCA | CCCTACCTAA | CCAACCCCCT | CCTCTCCCAT | 850 |
| CCTTACTAGC | CAAAGCCCTT | TCAACCCTTG | GGGCTTTTCC | TACACCTACA | 900 |
| CACCAGGGCA | ATTTAGAAC | TCATGGCTCT | CCTAGAAAAC | GCCTACCTCC | 950 |
| TTGGAGACTG | ACCCTCTACA | GTCCAGGAGG | CAGACACTCA | GACAGAGGAA | 1000 |
| CTCTGTCCTT | CAGTCGCGGG | AGTTCCAGAA | AGAGCCATAC | TCCCCTGCAG | 1050 |
| AGCTAACTAA | GCTGCCAGGA | CCCAGCCAGA | GCATCCCCCT | TTAGCCGAGG | 1100 |
| GCCAGCTCCC | CAGAATGAAA | AACCTGTCTG | GGGCCCCTCC | CTGAGGCTAC | 1150 |
| AGTCGCCAAG | GGGCAAGTTG | GACTGGATTC | CCAGCAGCCC | CTCCCACTCC | 1200 |
| GAGACAAAAT | CAGCTACCCT | GGGGCAGGCC | TCATTGGCCC | CAGGAAACCC | 1250 |
| CAGCCTGTCA | GCACCTGTTC | CAGGATCCAG | TCCAGCGCA | GTATGGCATC | 1300 |
| CACACTGCCT | GTCCAGACCT | TGCCCCTGAT | CCTGATTCTG | CTGGCTGTCC | 1350 |
| TGGCTCCGGG | GACTGCAGGT | CTCTATTGCT | GGTGGGTGCG | AGGAGGGTTT | 1400 |

```
CAGAGCGCTA GACAGGGAAC ATTGTCTCCC CAGGGCTCTC AAGGACAGGA      1450
ATGTTGGTCT AGCTGGTTGG GGTTGAGAGT TACTAGTGGT AGGAATCAGG      1500
TGACAAATTC CTGGGCTTCT TCCCAGATCC AGGAGTCAAG AAATTTGGGT      1550
AAGTGTCCAA GGTTTGTGTG AGTTGGGCGA GACTGGGGAC TGACTGGGTG      1600
CCATGGTCTA GTTTGGGTCG GTAGGGCTAT CTGGCTCCCA ACAGCGCGGC      1650
GTACCCACCA TCTGCAGATC AAGCCTGCCA TCTGGTGGTC AGATCCACAC      1700
GCTCCTCTTC TGTCTCTGCA CCCTTAGCAA TGACCACCCA CCCACCCCGC      1750
CAGCTCTGAG TTAAGAGGGG GCTAACTCCT GAGTTCCCTC TCGGCTCCCT      1800
AACAGACTTC AACATCTCAA GCCTCTCTGG TCTGCTGTCT CCGGCGCTAA      1850
CAGAAAGCCT GTTAATTGCC TTGCCCCCAT GTCACCTCAC GGGAGGTAAT      1900
GCCACATTGA TGGTCCGGAG AGCCAACGAC AGCAAAGGTA GACCTCCCTT      1950
GTACCCATTT ATTCTACTCG TCGTAACCCC TCTTAACGAT ACCCAAGAGC      2000
TGCCCGTTCT ACAAGAGTGG ACGCTAGAAT CTGATCTTGC CTTTCACTCC      2050
TATTTCCCCT CAGTGGTTAA GTCAGACTTT GTGGTGCCTC CATGTCGCGG      2100
GCGCAGGGAG CTTGTGAGCG TGGTGGACAG TGGGTCTGGC TACACCGTCA      2150
CAAGGCTCAG CGCATATCAG GTGACAAACC TAACACCAGG AACCAAATAC      2200
TAGTAGGTAC CGATGGACAC CTGTGGAGGT GGGATGGCAA AAAAGGGAAG      2250
TGGAGGTCCC GTGAGGGTGG GGAAGTGCCG GGAAGCATGA GTTAGAGAGG      2300
GCACAGCTAA AGGGTAGGAA ATGTGAACCT GGACCCCAGG AGGGCCCAGA      2350
TGGGACACAT AGCTAGAAGG TGGAGGCTGG AACCCCTCCT CCCGAGTGCC      2400
AGATACGTAC AACCTCTGCT TTCTCTCAAC TCCGCCTCTA AAGCATATCC      2450
TACCGAGTAC AGAAGGGGAC GTCGACCGAG TCCAGTCCAG AGACTCCCAT      2500
GTCCACGCTT CCTCGTTAAG TAAAATGCCC GTCTCTCACA CTTCCCTAAG      2550
CTCCGACTTT TTTCTCCTAG AGCAAGTTAG CTAAACTGTT TCCCGAGTGC      2600
TCAGTCGCAC ACACACCCCC TCCCCAACCC CCAGTATTT GGTATGGCCC       2650
CTCCTGTCCT GTTCAATCAT CTCTGCACTA GAGGTTCCTT GTGCAGAGGG      2700
ATGATGTCCT CCTTGGTGGC TCCTAAGTGT TGCTGTGAGG GGGGTCTATG      2750
TTTGCTTGAC TGGTTGGCTG GATGACCAGT TGAACTGATG CTGGAGGCTA      2800
CTGGATGGCT GGGCTAATGC TGTGAACCAC AGGAGCTACC TAGGAACCCC      2850
TTCAACTCAC AGAGGTTCCC CCATCTTCTT CTGACAGGAA AAAACATGGA      2900
GTCTATTGGG TTAGGAATGG CCCGGACAGG AGGGATGGTG GTCATCACAG      2950
TGCTGCTGTC TGTGGCCATG TTCCTGTTGG TCGTGGGTCT TATTGTTGCC      3000
CTGCACTGGG ATGCCCGCAA ATGAAAAGGG CTCTCCTGCA TCCCAGGCTC      3050
CTCCAAGAAG TCCAGCCTGC CTCCTGCCAG GCTGTAGTCA CTGGCTTCTC      3100
AGTGGCTTTT CTTCCCTCTC CCCGCCCCCT CCTCGAGTCC ACTCCTGACA      3150
GTGCCCCCTC CCTGCTCCCT GTCTCACCTT GCAGCACTCC CTGCTAGCCC      3200
CACTGCAATC CTGCCAACAC TGATTTATCT CTTAACTGTA CTTAATTCTC      3250
ACAATAAAGG CTGACCCACG TAGTATGTCT CATCTCCGAC CATGTCTATG      3300
TGAGTCACCC CTTTAGCTGG TCCCCTTATG CACATATCAA AACTACCAAT      3350
GTCAAGGTCA CGTGCATGTC ATTTTCTCTA TCCCAAACCC CAAGGGTGAC      3400
```

| | | | | | |
|---|---|---|---|---|---|
| TTTTACCAGG | AGGGAGGCAA | GCAGAGGCAG | AGATAATGAA | GCCTCAAGCC | 3450 |
| CAGACTAGGG | AAGCCCTCCA | AGCCCCAGAC | CTAGGGCTTG | GGTTTTGCAT | 3500 |
| CCTGCACTCA | GTAGATACCC | AAGCAGGAGT | CTAGTTGGGC | AGGGGGTAGA | 3550 |
| AGCTGGATCA | CCATGTGAGC | CTGACTGGGA | AGCTGACAGA | ACTAGGGAAG | 3600 |
| AACTAGAGAA | AACACAAACA | GGGCAGGCCC | TCCAGCCCTG | GGTGAAGAAC | 3650 |
| ATGCTAAACG | GTTCTAGACC | CCTAGAGCCG | AGGTGGACGG | AAGCTCCTGG | 3700 |
| AAGGGGGAGG | GGGGGACACA | ACATAGGTAA | ACAGGCAGTG | GCACCCTCGT | 3750 |
| CCATTTTTAA | AATATAGTTT | TGTTCTATAA | AAGTTTTATT | TATTTATTTA | 3800 |
| TTTGCTTGTT | TTTATTTGTT | TGTTTGTTTT | CCAGAGCTGA | GGCAAAAACC | 3850 |
| CAGGACCTTG | AGCTTGCTAG | GCAAGTGCTC | TACCACTGAG | CTAAATCCCC | 3900 |
| AACCCCTGTT | TTTGTTTTTT | TGAAGCAGGG | TTTCTCTGTG | TAGCTCTGGC | 3950 |
| TGTCCTAGAG | CTC | | | | 3963 |

(2) INFORMATION FOR SEQ ID NO: 2:

(i) SEQUENCE CHARACTERISTICS:
    (A) LENGTH: 11
    (B) TYPE: Amino Acid
    (D) TOPOLOGY: Linear (xi) SEQUENCE DESCRIPTION: SEQ ID NO: 2:

GLU  LEU  VAL  SER  VAL  VAL  ASP  SER  GLY  SER  GLY
        1               5                        10

What is claimed is:

1. A recombinant nucleic acid construct comprising a mouse UP-II promoter operatively linked to a heterologous gene wherein said promoter directs expression of said heterologous gene in the urothelium in vivo.

* * * * *